United States Patent
Chen et al.

(10) Patent No.: US 9,630,275 B2
(45) Date of Patent: Apr. 25, 2017

(54) METHODS AND DESIGNS FOR FORMING JOINTS BETWEEN METALLIC MEMBERS

(75) Inventors: Hancun Chen, Maple Grove, MN (US); Mike Sterud, Prescott, WI (US); Syed Naveed, Marlborough, MA (US); Verivada Chandrasekaran, Mercer Island, WA (US); Vitto Monni, Seattle, WA (US)

(73) Assignee: BOSTON SCIENTIFIC LIMITED, Hamilton (BM)

( * ) Notice: Subject to any disclaimer, the term of this patent is extended or adjusted under 35 U.S.C. 154(b) by 1269 days.

(21) Appl. No.: 12/635,542

(22) Filed: Dec. 10, 2009

(65) Prior Publication Data

US 2010/0176095 A1    Jul. 15, 2010

Related U.S. Application Data

(60) Provisional application No. 61/121,489, filed on Dec. 10, 2008.

(51) Int. Cl.
*B23K 26/211*    (2014.01)
*B23K 35/00*    (2006.01)
(Continued)

(52) U.S. Cl.
CPC .......... *B23K 35/001* (2013.01); *B23K 26/211* (2015.10); *B23K 26/32* (2013.01); *B23K 26/322* (2013.01); *B23K 26/323* (2015.10); *A61M 25/09* (2013.01); *A61M 2025/09108* (2013.01); *B23K 2201/34* (2013.01); *B23K 2203/05* (2015.10); *B23K 2203/14* (2013.01);
(Continued)

(58) Field of Classification Search
CPC .. B23K 35/327; B23K 10/02; B23K 2203/04; B23K 2203/14; B23K 2203/24; B23K 26/3233; B23K 35/3066
See application file for complete search history.

(56) References Cited

U.S. PATENT DOCUMENTS 2,985,747 A    5/1961    Kutchera
3,038,988 A    6/1962    Kessler
(Continued)

FOREIGN PATENT DOCUMENTS

EP    1584407 A1    10/2005
JP    6269961 A    9/1994

OTHER PUBLICATIONS

"Electronegativity", Web page <http://www.tutor-homework.com/Chemistry_Help/electronegativity_table/electronegativity.html>, 1 page, Mar. 8, 2008, retrieved from Internet Archive Wayback Machine, <https://web.archive.org/web/20080308143155/http://www.tutor-homework.com/Chemistry_Help/electronegativity_table/electronegativity.html> on Jun. 30, 2015.*
(Continued)

*Primary Examiner* — Andy Huynh
*Assistant Examiner* — Sitaramarao S Yechuri
(74) *Attorney, Agent, or Firm* — Seager, Tufte & Wickhem, LLP

(57) ABSTRACT

Disclosed are methods and structures for joining metallic members. A welding material can be used between two metallic members that comprise different metals. The different metals can normally form brittle intermetallic compounds when welded to one another, and the welding material can inhibit the formation of the brittle intermetallic compounds.

13 Claims, 12 Drawing Sheets

(51) Int. Cl.
  *B23K 26/322* (2014.01)
  *B23K 26/32* (2014.01)
  *B23K 26/323* (2014.01)
  *A61M 25/09* (2006.01)
  *B23K 103/24* (2006.01)
  *B23K 101/34* (2006.01)
  *B23K 103/00* (2006.01)
  *B23K 103/14* (2006.01)
  *B23K 103/04* (2006.01)
  *B23K 103/18* (2006.01)

(52) U.S. Cl.
  CPC ...... *B23K 2203/24* (2013.01); *B23K 2203/26* (2015.10); *B23K 2203/50* (2015.10)

(56) References Cited

U.S. PATENT DOCUMENTS

| | | | |
|---|---|---|---|
| 4,196,336 A * | 4/1980 | Smoller et al. | 219/76.15 |
| 4,281,235 A * | 7/1981 | Peloquin | 219/121.14 |
| 4,588,480 A | 5/1986 | Thoma | |
| 4,674,675 A | 6/1987 | Mietrach | |
| 4,708,282 A | 11/1987 | Johnsen et al. | |
| 4,842,182 A | 6/1989 | Szecket | |
| 4,976,529 A | 12/1990 | Segoshi et al. | |
| 5,106,010 A | 4/1992 | Stueber et al. | |
| 5,183,991 A * | 2/1993 | Arai | 219/121.64 |
| 5,213,111 A | 5/1993 | Cook | |
| 5,242,759 A | 9/1993 | Hall | |
| 5,341,818 A | 8/1994 | Abrams et al. | |
| 5,354,623 A | 10/1994 | Hall | |
| 5,358,796 A | 10/1994 | Nakamura et al. | |
| 5,368,049 A | 11/1994 | Raman | |
| 5,368,661 A | 11/1994 | Nakamura et al. | |
| 5,431,508 A | 7/1995 | Kitamura | |
| 5,452,028 A | 9/1995 | Iijima | |
| 5,488,959 A | 2/1996 | Ales | |
| 5,695,111 A | 12/1997 | Nanis et al. | |
| 5,733,667 A | 3/1998 | Nakasuji et al. | |
| 5,741,818 A | 4/1998 | Dimmock | |
| 5,772,105 A | 6/1998 | Zadno-Azizi et al. | |
| 5,858,556 A | 1/1999 | Eckert et al. | |
| 6,234,981 B1 | 5/2001 | Howland | |
| 6,326,089 B1 | 12/2001 | Claxton | |
| 6,329,069 B1 | 12/2001 | Azizi et al. | |
| 6,379,392 B1 | 4/2002 | Walak | |
| 6,386,428 B2 | 5/2002 | Claxton | |
| 6,410,165 B1 | 6/2002 | Warren et al. | |
| 6,488,637 B1 | 12/2002 | Eder et al. | |
| 6,520,923 B1 | 2/2003 | Jalisi | |
| 6,554,854 B1 | 4/2003 | Flanagan | |
| 6,592,670 B1 | 7/2003 | Gochnour | |
| 6,602,228 B2 | 8/2003 | Nanis et al. | |
| 6,613,452 B2 | 9/2003 | Weir | |
| 6,730,876 B2 | 5/2004 | Copeland et al. | |
| 6,849,085 B2 | 2/2005 | Marton | |
| 6,866,730 B2 | 3/2005 | Cheng et al. | |
| 6,875,949 B2 | 4/2005 | Hall | |
| 6,918,882 B2 | 7/2005 | Skujins et al. | |
| 6,935,404 B2 | 8/2005 | Duerig et al. | |
| 6,953,146 B2 | 10/2005 | Nanis | |
| 7,074,197 B2 | 7/2006 | Reynolds et al. | |
| 2002/0170888 A1 * | 11/2002 | Lehmann et al. | 219/121.46 |
| 2003/0009208 A1 | 1/2003 | Snyder et al. | |
| 2003/0060732 A1 | 3/2003 | Jacobsen et al. | |
| 2003/0069522 A1 | 4/2003 | Jacobsen et al. | |
| 2004/0181174 A2 | 9/2004 | Davis et al. | |
| 2004/0182835 A1 | 9/2004 | Hall | |
| 2005/0142377 A1 * | 6/2005 | Hall | 428/660 |
| 2006/0047223 A1 | 3/2006 | Grandfield | |

OTHER PUBLICATIONS

Miyamoto, Yoshinari et al., "Freeform Fabrication of Intermetallic Alloys by 3D Micro Welding", Transactions of JWRI, vol. 34, 2005.
Townsend, Greg, "Stainless Steel & Nitnol & the Oxide Film relating to Welding", Fishing dot com, Sep. 2009.
"Science & Technology USSR: Materials Science", Foreign Broadcast Information Service, Apr. 27, 1988.
"Welding Nitinol to Ferrous Metals". EWI Joining Innovation.

* cited by examiner

METHODS AND DESIGNS FOR FORMING JOINTS BETWEEN METALLIC MEMBERS

RELATED APPLICATIONS

This application claims priority to Provisional Patent Application 61/121,489, filed Dec. 10, 2008, the entire disclosure of which is incorporated herein by reference.

TECHNICAL FIELD

This disclosure pertains generally to methods and designs for connecting metallic members. Specifically, the disclosure can pertain to methods and designs for connecting metallic members to one another within medical devices.

BACKGROUND

Joining of metal members is performed for many different purposes. In some contexts, the metal members being joined can comprise different metals. As an example, metals can be used in the construction of medical devices, and in some cases two metal members that comprise different metals are joined to one another within a medical device. There is an ongoing need for methods and designs to improve the strength and/or durability and/or other properties of the joint between such metallic structures.

SUMMARY

The disclosure describes several alternative designs, materials and methods of providing a joint between two metallic structures. In each embodiment, a weld material interposed between the surfaces to be joined reduces the concentration of brittle intermetallic compounds present within the weld region following the formation of the weld joint relative to the amount which would be present in the absence of the weld material.

Accordingly, in one example embodiment a method of manufacturing a medical device can include providing a first and a second metallic member. Each of the metallic members can have a welding surface. The welding surfaces can be the surfaces of the metallic members that are to be welded to one another. For example, the metallic members can be elongate metallic members and the welding surfaces can be located on a distal portion (e.g., the distal end) of one metallic member and a proximal portion (e.g., the proximal end) of the other metallic member. The metallic members can comprise different metals. In some examples, the metallic members can comprise metals that can form brittle intermetallic compounds with one another when welded.

In some embodiments, a welding material can be applied to one or both of the welding surfaces. If the metallic members comprise metals that can form brittle intermetallic compounds when welded, some welding materials can inhibit the formation of the brittle intermetallic compounds in the weld joint. The welding surfaces and the welding material can then be welded together, for example using a heat source such as a laser. In some cases, the first metallic member can comprise iron and the second metallic member can comprise titanium. For example, the first metallic member could comprise stainless steel or another iron-comprising alloy and the second metallic member could comprise a nickel-titanium alloy, such as Nitinol, or another titanium-comprising alloy.

Some example embodiments may relate to a method of forming a weld joint, and may include providing a first metallic member comprising a first alloy comprising iron, the first member having a first welding surface, and providing a second metallic member comprising a second alloy comprising titanium, the second member having a second welding surface. A welding material may be applied to at least one of the welding surfaces. The welding surfaces and the welding material may be welded to form a joint between the first and second metallic members, and the welding material may inhibit the formation of the brittle intermetallic iron-titanium compounds within the joint.

Another example embodiment relates to a medical device comprises first and second metallic members with a joint disposed between the metallic members. The two metallic members can comprise two different metals. In some cases these different metals, if joined directly to one another through welding, can form brittle intermetallic compounds. The weld joint can comprise metal from the first metallic member, metal from the second metallic member, and a welding material. If the metallic members comprise metals that may normally form brittle intermetallic compounds when welded, the welding material can inhibit the formation of the intermetallic compounds.

For example, one embodiment relates to a medical device comprising a first metallic member comprising a first alloy including iron, a second metallic member comprising a second alloy including titanium, wherein the first and second alloy are different. A weld joint is disposed between the welding surfaces of the first and second metallic members, the joint comprising the first alloy, the second alloy, and a welding material. In some embodiments, the medical device may include a first elongate stainless steel member, a second elongate nickel-titanium alloy member, and a weld joint formed between the first and second elongate members, the joint comprising components of stainless steel, nickel-titanium alloy, and a welding material.

In some embodiments, the welding material may comprise carbon, nitrogen, gold, or combinations thereof. For example, in some embodiments, the welding material can comprise and/or consist essentially of carbon (e.g. graphite) and/or carbon-containing materials in a solid or liquid state with a proper range of viscosity. In some embodiments, the carbon-containing material can be an organometallic compound or complex (e.g. $FeC_2O_4 \cdot 2H_2O$, $Fe(OOC_7H_{15})(OC_3H_7)$), an organic compound consisting essentially of carbon, hydrogen, and oxygen, a metal carbide wherein the affinity of the metal for carbon is weaker than the affinity of titanium for carbon, or an alloy containing at least one such metal carbide or sufficient amount of carbon. In some embodiments, for example, if graphite is used as the carbon containing material, it can be applied to the welding surfaces in the form of a sheet or paste. In such examples, the joint can comprise titanium carbide.

In some examples, the welding material can comprise and/or consist essentially of pure nitrogen (e.g. nitrogen gas), and/or nitrogen-containing materials in a solid or liquid state with a proper range of viscosity. In some examples, the nitrogen-containing material can be a nitrogen containing organometallic compound or complex (e.g., $Fe(NO_3)_3 \cdot 9H_2O$), an organic consisting essentially of carbon, nitrogen, hydrogen, and oxygen, a metal nitride wherein the affinity of the metal for nitrogen is weaker than the affinity of titanium for nitrogen, or an alloy containing at least one such metal nitride, or sufficient amount of nitrogen. If nitrogen gas is used, it may be applied in an enclosure placed over the welding area. In these examples, the joint can comprise titanium nitride.

In some examples, the welding material may comprise and/or consist essentially of a combination and/or mixture of carbon and/or a carbon-containing material and nitrogen and/or a nitrogen-containing material. The welding material can also be an organometallic compound or complex containing carbon and nitrogen (e.g. $Fe_4[Fe(CN)_6]_3$), an organic consisting essentially of carbon, nitrogen, hydrogen, and oxygen, a metal carbonitride with which affinity of the metal for carbon and/or nitrogen is weaker than that of titanium for carbon and/or nitrogen, or an alloy containing at least one such metal carbonitride or sufficient amount of carbon and nitrogen. In such case the joint may comprise titanium carbonitride and/or a mixture of titanium carbide, titanium nitride, and/or titanium carbonitride.

In yet some other embodiments, the welding material may comprise and/or consist of gold and/or a mixture of gold and nickel.

The above summary of some embodiments is not intended to describe each disclosed embodiment or every implementation of the present invention. The Figures, and Detailed Description which follows, more particularly exemplify these and other embodiments.

BRIEF DESCRIPTION OF THE FIGURES

The invention may be more completely understood in consideration of the following detailed description of various embodiments of the invention in connection with the accompanying drawings, in which.

Figure 1:
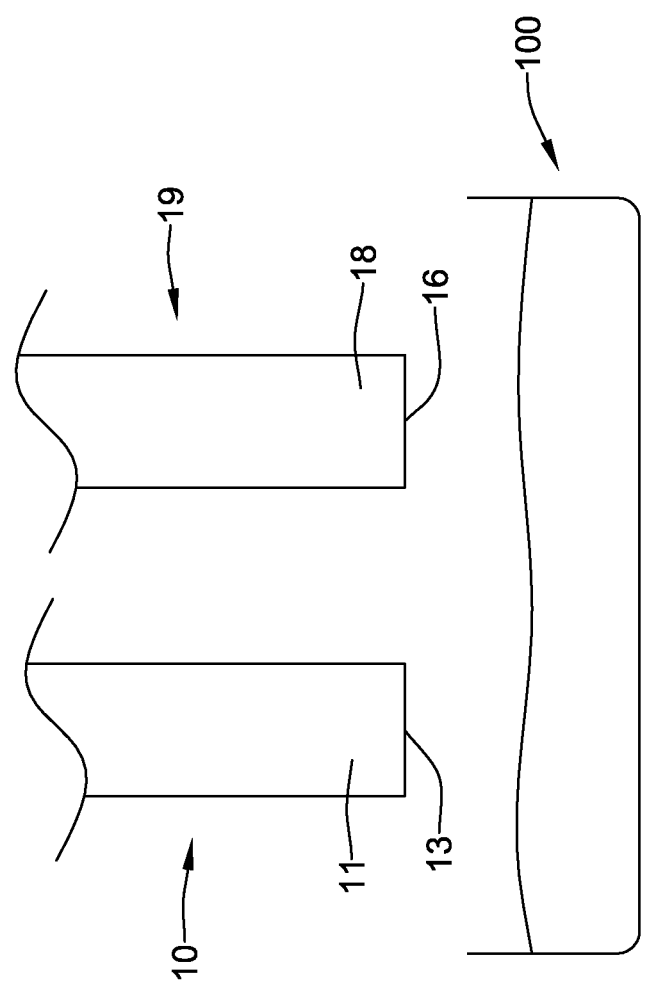
FIG. 1 shows two elongate structures before coating with a welding material and a coating bath into which the elongate structures can be dipped.

While the invention is amenable to various modifications and alternative forms, some specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention.

DETAILED DESCRIPTION OF SOME EMBODIMENTS

For the following defined terms, these definitions shall be applied, unless a different definition is given in the claims or elsewhere in this specification.

The term "polymer" will be understood to include polymers, copolymers (e.g., polymers formed using two or more different monomers), oligomers and combinations thereof, as well as polymers, oligomers, or copolymers that can be formed in a miscible blend by, for example, coextrusion or reaction, including transesterification. Both block and random copolymers are included, unless indicated otherwise.

All numeric values are herein assumed to be modified by the term "about", whether or not explicitly indicated. The term "about" generally refers to a range of numbers that one of skill in the art would consider equivalent to the recited value (i.e., having the same function or result). In many instances, the terms "about" may include numbers that are rounded to the nearest significant figure.

The recitation of numerical ranges by endpoints includes all numbers within that range (e.g., 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

It is noted that references in the specification to "an embodiment", "some embodiments", "other embodiments", etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it would be within the knowledge of one skilled in the art to effect such feature, structure, or characteristic in connection with other embodiments whether or not explicitly described.

The following description should be read with reference to the drawings wherein like reference numerals indicate like elements throughout the several views. The drawings, which are not necessarily to scale, depict illustrative embodiments of the claimed invention.

Joining of metals is performed for many different purposes. In some cases, the metal members being joined can comprise different metals. In any case, it can be desirable for the joint between the two metallic members to have certain properties, such as high strength and/or durability and/or low brittleness.

In some cases, the two metallic members can comprise two different metals that, if welded directly to one another, can form intermetallic compounds. Some of these intermetallic compounds can affect the properties of the joint between the two metallic members, for example the intermetallic compounds can be brittle relative to the metallic members being joined.

In some cases, one of the metallic members can comprise titanium (for example, it could comprise a nickel-titanium alloy, such as Nitinol or other alloys comprising titanium) and the other metallic member can comprise iron (for example, it could contain stainless steel or other alloys comprising iron). When these materials are joined to one another, a brittle intermetallic compound can form (for example, FeTi or $Fe_2Ti$). The formation of such an intermetallic compound can lead to a relatively low strength, low durability joint between the metallic members. For instance, the intermetallic compounds could cause the joint between the metallic members to be more brittle than the metallic members being joined, thus forming a joint that can be more likely to break when the joint has a strain placed on it.

In one example embodiment, a welding material can be used in order to enhance the desired properties of the joint between the metallic members. In cases where the different metals of the two metallic members can form brittle intermetallic compounds, the welding material can inhibit (e.g., substantially completely prevent) the formation of the intermetallic compounds. Without being bound by any particular theory, it is thought that this process is facilitated by the fact that elements or compounds in certain welding materials can react or otherwise bind with a precursor to the intermetallic compound (e.g., titanium), preventing the precursor from reacting with another metal (e.g., iron), thus inhibiting the production of brittle intermetallic materials. As a result, the presence of such welding materials in a joint between two metallic members can lead to a stronger and/or more durable and/or less brittle joint. In other embodiments, it is thought that the elements or compounds in certain welding materials or reaction products formed therewith during the welding process may act as diffusional or dilutional barriers which tend to limit mixing of the components of the metallic members which otherwise would react to form brittle intermetallic compounds. In yet other embodiments, it is thought that both of these mechanisms may contribute to a reduced concentration of brittle intermetallic compounds being present within the weld joint.

Examples of welding materials that can inhibit and/or prevent the formation of intermetallic compounds are materials comprising carbon, materials comprising nitrogen, materials comprising both carbon and nitrogen, materials comprising gold, and materials comprising gold and nickel.

In some examples, the welding material can comprise and/or consist essentially of carbon (e.g. graphite) and/or carbon-containing materials in a solid or liquid state with a proper range of viscosity. In some embodiments, the carbon-containing material can be an organometallic compound or complex (e.g. $FeC_2O_4 \cdot 2H_2O$, $Fe(OOC_7H_{15})(OC_3H_7)$), an organic consisting essentially of carbon, hydrogen, and oxygen, a metal carbide wherein the affinity of the metal for carbon is weaker than the affinity of titanium for carbon, or an alloy containing at least one such metal carbide or sufficient amount of carbon. In some embodiments, for example, if graphite is used, it can be applied to the welding surfaces in the form of a sheet or foil or paste or coating. In such examples, the joint can comprise titanium carbide.

In some examples, the welding material can comprise and/or consist essentially of pure nitrogen (e.g. nitrogen gas), and/or nitrogen-containing materials in a solid or liquid state with a proper range of viscosity. In some examples, the nitrogen-containing material can be an organometallic compound or complex (e.g., $Fe(NO_3)_3 \cdot 9H_2O$), an organic consisting essentially of carbon, nitrogen, hydrogen, and oxygen, a metal nitride wherein the affinity of the metal for nitrogen is weaker than the affinity of titanium for nitrogen, or an alloy containing at least one such metal nitride or sufficient amount of nitrogen. If nitrogen gas is used, it may be applied in an enclosure placed over the welding area. In these examples, the joint can comprise titanium nitride.

In some examples, the welding material may comprise and/or consist essentially of a mixture of carbon or a carbon-containing material and nitrogen or a nitrogen-containing material. The welding material can also be a carbon- and nitrogen-containing organometallic or complex (e.g. $Fe_4[Fe(CN)_6]_3$), an organic consisting essentially of carbon, nitrogen, hydrogen, and oxygen, a metal carbonitride wherein the affinity of the metal for carbon and nitrogen is weaker than the affinity of titanium for carbon and nitrogen, or an alloy containing at least one such metal carbonitride or sufficient amount of carbon and nitrogen. In such case, the joint may comprise titanium carbonitride, titanium carbide, or titanium nitride.

As indicated above, suitable welding materials may also comprise gold or gold alloys, or a combination of gold or gold alloys and nickel or nickel alloys. For example, a layer of gold and/or a layer of gold and a layer of nickel may be disposed on one or more of the welding surfaces to act as the welding material. In some embodiments, for example, a layer of gold may be deposited on one or more of the welding surfaces through a strike and/or plating process, or other suitable application techniques, and the layer of gold may act as a suitable welding material. In some embodiments, an additional layer of nickel may be applied over the layer of gold, for example, through a strike and/or plating process, and the gold and nickel layers may act as a suitable welding material. In yet other embodiments, it is contemplated that a layer including a mixture of gold and nickel could be applied to the welding surfaces, and act as a suitable welding material. Further, it is also contemplated that welding materials may also comprise any combination of the above welding materials discussed herein.

In some cases, it is desirable to control the amount of welding material and its composition in order to provide for the desired properties in the bond. Without being bound by the theory, it is thought that certain elements or compounds have an affinity to bond with titanium (or other precursors to intermetallic compounds). When these elements or compounds bond with titanium (or other precursor), the resulting compound does not have as much of a negative effect on the properties of the bond as do the intermetallic compound that would otherwise form. However, if too much of the welding material is added, the welding material can bond with all of the available titanium (or other precursor), and portions of the welding material can remain. This remaining welding material can in some cases have a deleterious effect on the properties of the weld.

For example, in cases of titanium and iron, the welding material may react with all of the available titanium, producing compounds that can have little negative effect on the weld properties. If too much welding material is present, however, the remaining welding material can react with the iron, producing compounds that have a negative effect on the weld properties. Thus, controlling the amount of the welding material can be important in order to obtain the desired weld properties. One of ordinary skill in the art would recognize that the composition of the metallic members being joined (the type and quantity of metals in the metallic members), the shapes and/or contact area between the metallic members, and the composition of the welding material, among other factors, can affect the amount and composition of the welding material that is required.

In one example embodiment, a method of forming a joint can comprise providing a first and a second metallic member (for example, elongate metallic members). The first and second metallic members can have first and second welding surfaces, respectively. The welding surfaces can be the surfaces that are being welded to one another. One or both of the first and second welding surfaces can be coated with a welding material. The welding surfaces with the welding material on one or both of the welding surfaces can be placed in close proximity (e.g., they can be placed with a very small gap between them or they can be touching one another), and the welding surfaces and the welding material can be welded to one another. The welding step can be performed using any suitable heat source, for example a laser. The welding can cause the welding material and in some cases portions of the welding surfaces to melt. In some embodiments, the molten welding material and welding surfaces can flow together and, when they cool and solidify, they can form a joint between the metallic members. In this example, the welding material and the materials of construction for the metallic members can be similar to any of the embodiments described herein. Also, it is noted that this method can be used in the manufacture of medical devices.

In another example embodiment, a device (e.g., a medical device) can comprise first and second metallic members (for example, an elongate metallic member). The two metallic members can be similar in composition to any of the metallic members described herein. A joint can be formed between the metallic members, and the joint can comprise metal or metals of the first metallic member, metal or metals from the second metallic member, and any of the welding materials described herein. Also, when the welding material comprises carbon and one of the metallic members comprises titanium, the joint can comprise titanium carbide. If the welding material comprises nitrogen and one of the metallic members comprises titanium, the joint can comprise titanium nitride. If the welding material comprises carbon and nitrogen and one of the metallic members comprises titanium, the joint may comprise titanium carbonitride, titanium carbide, or titanium nitride. It will be appreciated that some reactive metals in addition to, or instead of, titanium which are capable of forming brittle intermetallic compounds may be substituted for titanium in the discussion above.

Turning to FIG. 1, first and second elongate metallic members (10, 19) are shown along with a coating bath 100. The first and second elongate members can be similar in composition to any of the metallic members discussed herein. A distal portion 11 of the first metallic member 10 and a proximal portion 18 of the second metallic member 19 are shown. The first metallic member also has a distal end 13 disposed in the distal portion 11 and the second metallic member has a proximal end 16 disposed in the proximal portion 18. Also shown in FIG. 1 is one possible method for disposing a coating of welding material on the metallic members. Depicted is a coating bath, for example an electrodeposition or electroplating bath that may be used to apply a plate or strike of welding material, in which the distal portion 11 and the proximal portion 18 can be dipped.

The welding materials mentioned in this application can also be disposed on the distal portion 11 and the proximal portion 18 in other ways. For example, the coating could be disposed using a tinning process, a vapor deposition process, a dip-coating process, applying a gel or paste that contains the welding material, spray application, such as liquid spray, thermal spray, and cold spray, micropen coat method, roll coat method, sponge coat method, physical vapor deposition, sol-gel method, or the like, or using other suitable processes.

The distal and proximal portions (11, 18) can comprise welding surfaces. The welding surfaces can generally be the surfaces that are to be welded to one another. For example, in this embodiment, the welding surfaces can be the distal and proximal ends (13, 16). The welding surfaces can be coated with the welding material. For example, the welding material can be coextensive with the welding surface, the welding material can cover less than the entire welding surface, or the coating can extend across the entire welding surface and extend further outside of the welding surface. In addition, the welding material can be coated on one or both of the welding surfaces.

Figure 2:
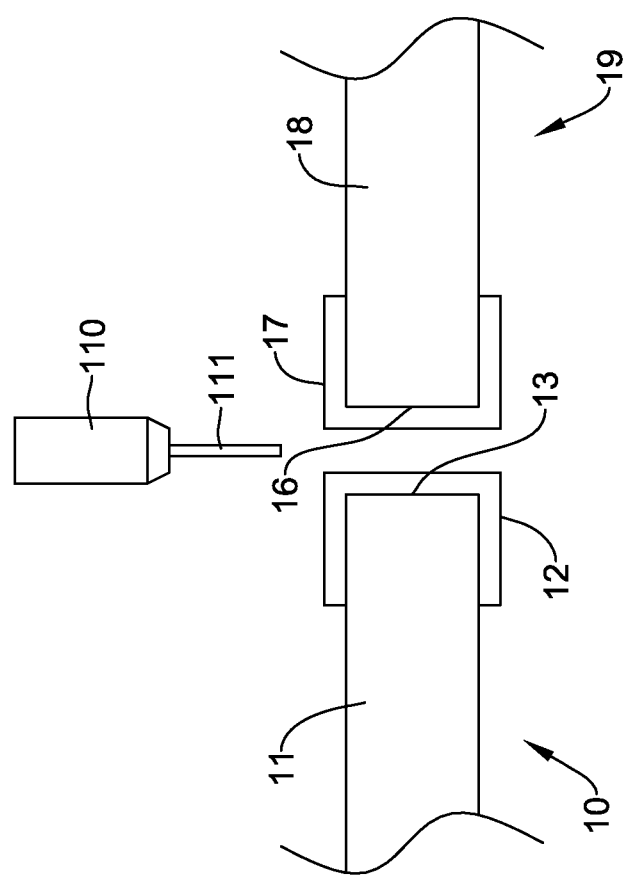
FIG. 2 shows the elongate members of FIG. 1 after they have been coated with welding material and a laser directed at the coated surfaces.

In FIG. 2, both welding surfaces (shown on ends 13, 16) have been coated. The coating thickness in some example applications can be in the range of about 0.01 micrometer to about 1000 micrometers, in some cases, in the range of about 1 micrometer to about 100 micrometers, and in some instances, in the range of about 5 and 50 micrometers. As shown in FIG. 2, the coating can extend across the entire welding surface and extend further outside the welding surface; here, the coating extends proximally for a distance along a portion of the distal portion 11 and distally for a distance along a portion of the proximal portion 18. The coated welding surfaces can be placed in close proximity to one another. (In this application, the phrase "coated welding surfaces" can include the embodiments where one surface is coated and one surface is uncoated.) "Close proximity" can include positioning the coated welding surfaces slightly apart as shown in FIG. 2, or placing the coated welding surfaces in contact with one another. Further, the coated welding surfaces can be pushed against one another.

With the metallic members placed in close proximity or being pushed against one another, the metallic members and the welding material can be welded together. In one embodiment, and as shown in FIG. 2, a laser 110 that can emit a laser beam 111 can be used to heat the welding material, and in some cases the welding surfaces. In some embodiments, the welding material can be melted by the heat source. In other embodiments, a portion of the welding surfaces can also be melted by the heat source. The molten materials can flow together, and, upon cooling and solidification, can form a joint between the first and second metallic members.

Figure 3:
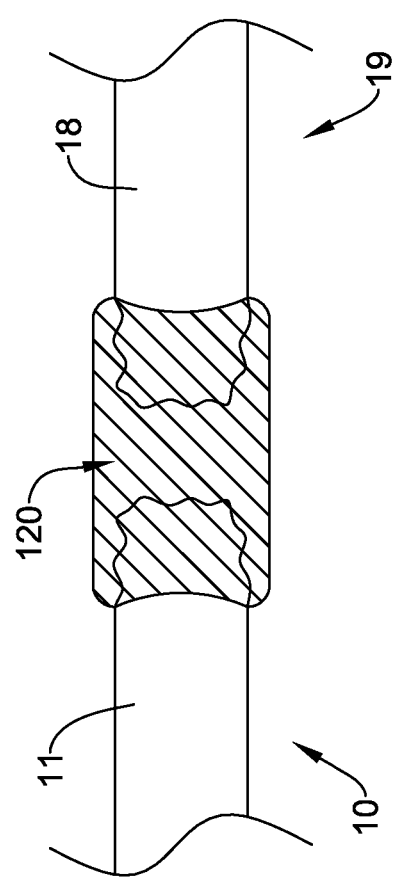
FIG. 3 shows the elongate members of FIGS. 1 and 2 after they have been joined to one another in a butt weld configuration.

An example of a joint between the first and second metallic members is shown in FIG. 3. In this Figure, the distal end of the first elongate metallic member 10 has been joined to the proximal end of the second elongate metallic member 19 at joint 120. Such a joint can be referred to as a butt joint. The joint 120 can comprise the welding material. In some cases, the joint can comprise metal or metals from the first elongate member and metal or metals from the second elongate member. In embodiments where the metals of the first and second elongate metallic members can form undesirable brittle intermetallic compounds, the welding material can inhibit (e.g., reduce, relative to that normally formed) the formation of such intermetallic compounds, and may in some cases substantially entirely prevent the formation of such intermetallic compounds. As mentioned above, some welding materials can bond with one of the precursors to the intermetallic compounds, thus preventing the formation of the intermetallics. As an example, carbon or nitrogen, or both, from certain welding materials can react with titanium, essentially binding the titanium and preventing it from reacting with iron. In such a case, the joint can comprise titanium nitride and/or titanium carbide and/or titanium carbonitride, or mixtures thereof.

In some embodiments, and as shown in FIG. 3, the joint 120 can have a larger outer diameter than the outer diameter of the metallic members (10, 19). In such a case, the outer diameter of the joint 120 can be at least in part formed by the welding material that was deposited outside the welding surfaces. In other cases, the joint 120 can follow the profile of the metallic members (10, 19). For example, this profile can occur when the welding material is disposed coextensively with the welding surface(s) or the welding material is disposed on less than the entire welding surface(s).

Figure 4:
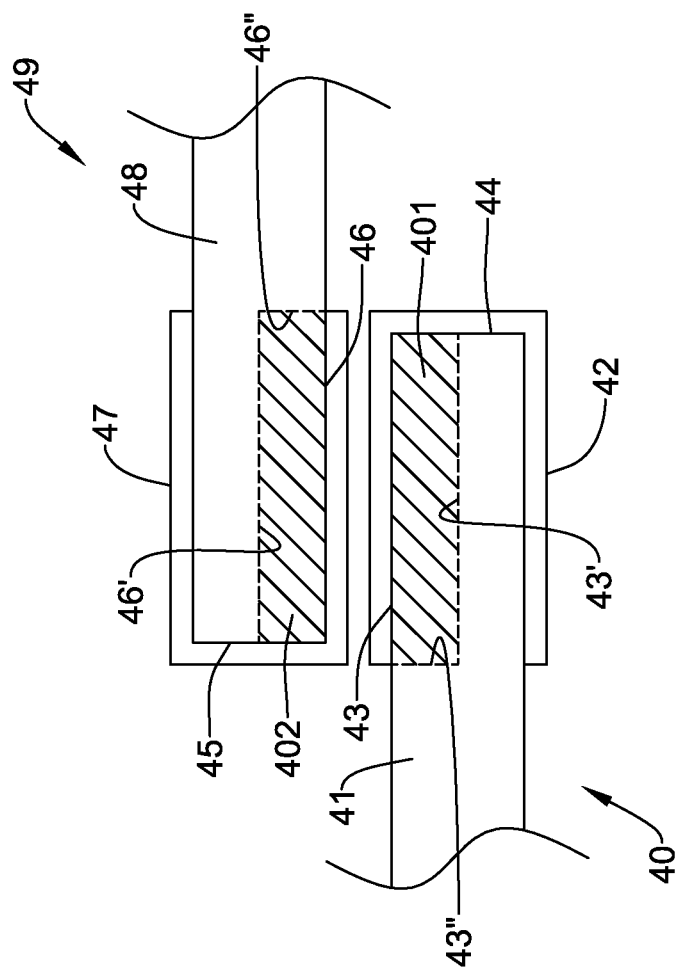
FIG. 4 shows two elongate structures before being joined to one another in a lap weld configuration.

FIG. 4 shows another embodiment of a method of forming a joint. A first elongate member 40 has a distal portion 41 with a distal end 44. A welding surface 43 is shown on one side of a portion of the distal portion 41. The welding surface 43 is also coated with a welding material 42. As shown, the welding material 42 can coat more than just the welding surface 43; in this case, the welding material 42 is shown as completely coating a distal region of the distal portion 41. As mentioned above with respect to FIGS. 1 and 2, the welding material 42 could also be disposed over less than the entire welding surface 43 or be coextensive with the welding surface 43. Also shown is a second elongate member 49 with a proximal portion 48 with a proximal end 45. A welding surface 46 is shown on one side of a portion of the proximal portion 48. The welding surface 46 is also coated with a welding material 47. As shown, the welding material 47 can coat more than just the welding surface 46; in this case, the welding material 47 is shown as completely coating a proximal region of the proximal portion 48. As mentioned above with respect to FIGS. 1 and 2, the welding material 47 could also be coated over less than the entire welding surface 46 or be coextensive with the welding surface 46. The welding materials (42, 47) of this Figure can be any of the welding materials mentioned in this application. Further, the metallic members (40, 49) can have a composition similar to any of the metallic members described herein. It is also contemplated that only one of the welding surfaces can be coated with a welding material.

In FIG. 4, as discussed with respect to FIG. 2, the coated welding surfaces (43, 46) can be placed in close proximity with one another and welded together. The joint that is formed between the first and second metallic members (40, 49) can be similar in composition and method of formation to the butt joint described with respect to FIG. 3. The joint formed by the configuration shown in FIG. 4 can be referred to as a lap joint.

FIG. 4 also shows some additional possible embodiments of a method for forming a joint between the first and second metallic members (140, 149). Specifically, FIG. 4 shows in phantom some cross-sections (401, 402) that can be removed from the distal portion 41 and the proximal portion 48. These cross-sections can be formed to complement one another so that they can be fit together. In such as case, the welding surface can be shown by reference numerals 43' and 43" for the first metallic member 40 and by 46' and 46" for the second metallic member 49. Other complimentary cross-sectional shapes could also be used. For example, some of the shapes that are shown in U.S. Pat. No. 6,488,637 to Eder et al. can be used, which is herein incorporated by reference in its entirety.

Figure 4A:
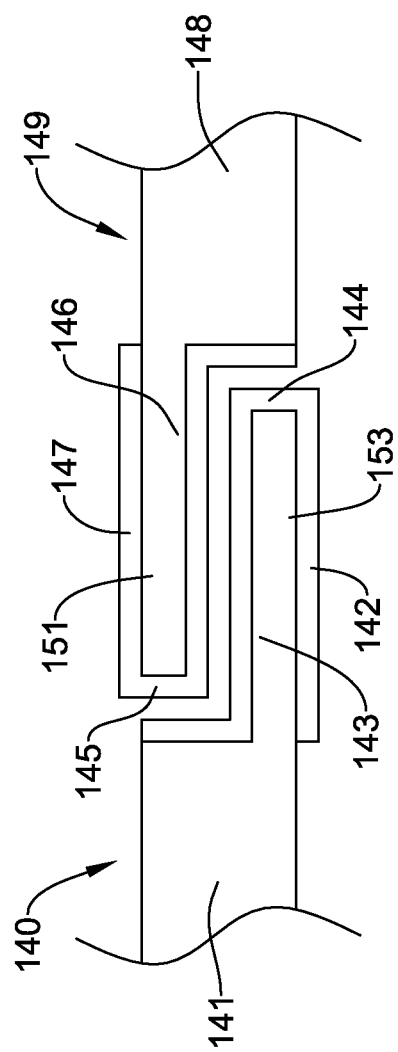
FIG. 4A shows two elongate structures before being joined to one another in a hybrid lap/butt weld configuration.

For example, FIG. 4A shows such an example configuration, wherein the first and second elongate members 140/149 include ends with mating geometries to provide for a joint that may be referred to an a hybrid lap/butt joint. The first elongate member 140 has a distal portion 141 with a distal end 144, and the distal portion 141 includes a stepped down geometry portion 151. A welding surface 143 is shown on one side of the portion 151. The welding surface 143 is also coated with a welding material 142. As shown, the welding material 142 can coat more than just the welding surface 143; in this case, the welding material 142 is shown as completely coating a distal region of the distal portion 141. As mentioned above with respect to FIGS. 1 and 2, the welding material 142 could also be disposed over less than the entire welding surface 143 or be coextensive with the welding surface 143. Also shown is a second elongate member 149 with a proximal portion 148 with a proximal end 145, and the proximal portion 148 includes a stepped down geometry portion 153. A welding surface 146 is shown on one side of a portion of the portion 153. The welding surface 146 is also coated with a welding material 147. As shown, the welding material 147 can coat more than just the welding surface 146; in this case, the welding material 147 is shown as completely coating a proximal region of the proximal portion 148. As mentioned above with respect to FIGS. 1 and 2, the welding material 147 could also be coated over less than the entire welding surface 146 or be coextensive with the welding surface 146. The welding materials (142, 147) of this Figure can be any of the welding materials mentioned in this application. Further, the metallic members (140, 149) can have a composition similar to any of the metallic members described herein. It is also contemplated that only one of the welding surfaces may be coated with a welding material.

In FIG. 4A, as discussed with respect to FIG. 2, the coated welding surfaces (143, 146) can be placed in close proximity with one another and welded together. The joint that is formed between the first and second metallic members (140, 149) can be similar in composition and method of formation to the butt joint described with respect to FIG. 3. The joint formed by the configuration shown in FIG. 4A can be referred to as a hybrid lap/butt joint.

Figure 5:
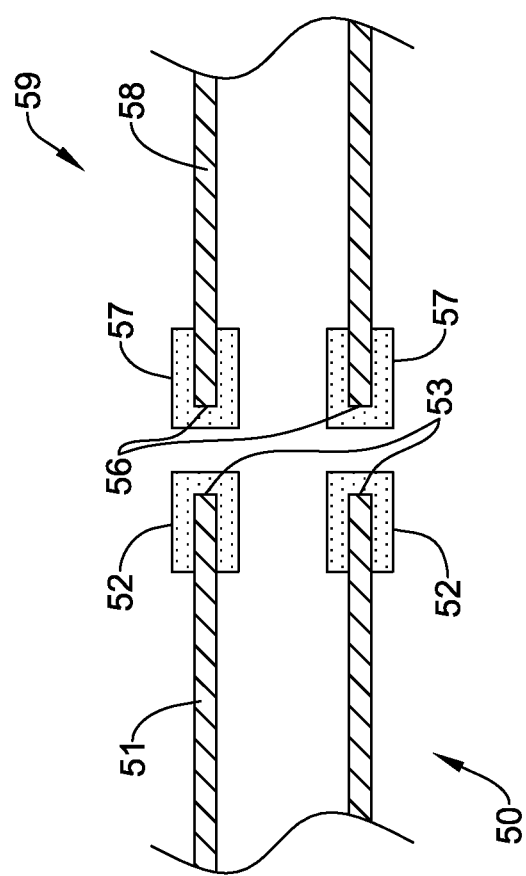
FIG. 5 shows two tubular elongate structures before being joined to one another in a butt weld configuration.

Turning to FIG. 5, first and second metallic members (50, 59) are shown in cross-section. In this example, the metallic members are tubular. First metallic member 50 can have a distal portion 51 with a distal end 53. The metallic member 50 can also have a welding surface; as shown in this figure, the welding surface can be the surface of the distal end 53. A welding material 52 can be disposed on the welding surface 53. The second metallic member 59 can have a proximal portion 58 with a proximal end 56. The second metallic member 59 can also have a welding surface; as shown in FIG. 5, the welding surface can be the surface of the proximal end 56. Welding material 57 can be disposed on the welding surface 56. The welding material can be disposed on less than the entire welding surfaces, it can be coextensive with the welding surfaces, or, as shown in FIG. 5, it can be disposed on more than the welding surface. Further, the welding material (52, 57) can be disposed on one or both welding surfaces (53, 56). The welding material can comprise any of the welding materials mentioned herein, and the metallic members can comprise materials similar to any of the metallic members mentioned herein.

Similar to the process shown in FIGS. 1-3, the coated welding surfaces (53, 56) can be placed in close proximity to one another and welded together. With the welding surfaces (53, 56) being located on the ends of the metallic members, the joint that is formed between the metallic members can be referred to as a butt joint.

Figure 6:
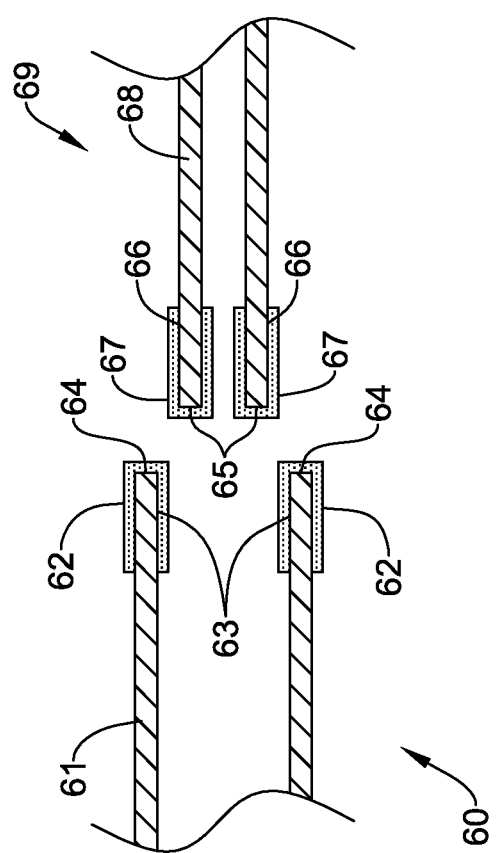
FIG. 6 shows two tubular elongate structures before being joined to one another in a lap weld configuration.

In FIG. 6, cross-sections of two tubular elongate metallic members (60, 69) are shown. A first member 60 has a distal portion 61 including the distal end 64 of the tubular member 60. Welding surface 63 is shown on the inside surface of the tubular member 60. Welding material 62 can be coated over the welding surface 63. A second member 69 has a proximal portion 68 including the proximal end 65 of the tubular member 69. Welding surface 66 is shown on the outside surface of the tubular member 69. A welding material 67 can be disposed over the welding surface 66. As mentioned with respect to other figures, the welding material (62, 67) can be disposed over less than the entire welding surface (63, 66), or it can be coextensive with the welding surface (63, 66). In addition, as shown in FIG. 6, the welding materials (62, 67) can cover more than the welding surfaces (63, 66). The welding material of 62 covers the inside and the outside surfaces of a distal region of the distal portion 61, and the welding material 67 covers the inside and outside surfaces of a proximal region of the proximal portion 68. The welding material shown in FIG. 6 can be disposed on either one, or both (as shown), of the elongate tubular metallic members (60, 69). The welding materials (62, 67) can comprise any of the welding materials that have been mentioned herein. Also, the metallic members (60, 69) can comprise any of the materials that were mentioned in conjunction with the other metallic members described herein.

Also, the elongate metallic tubular members (60, 69) can be brought into close proximity (here, this can be done by placing the second tubular member 69 at least partially inside the first tubular member 60). The first and second tubular members (60, 69) can then be welded together, for example using any of the techniques described with respect to FIGS. 1-3. With some overlap between the first member distal portion 61 and the second member proximal portion 68, the joint can be referred to as a lap joint.

Figure 7:
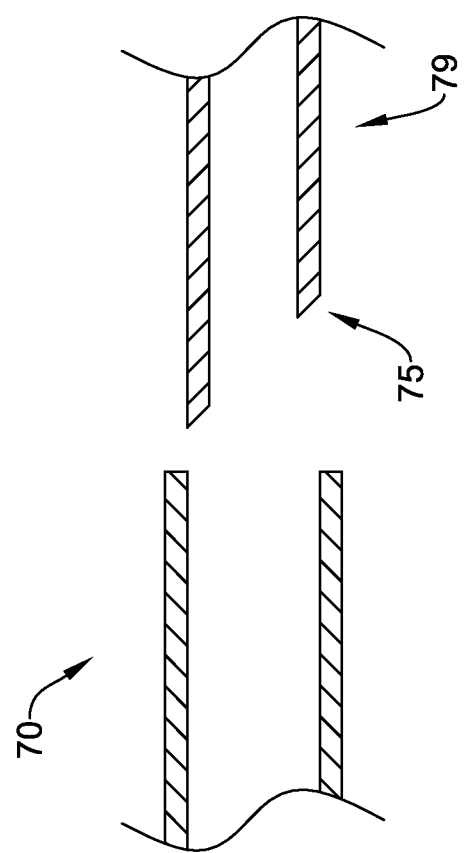
FIG. 7 shows two tubular elongate structures before being joined together where the tubular elongate members are sized and shaped to facilitate the insertion of one tubular elongate member into the other tubular elongate member.
Figure 8:
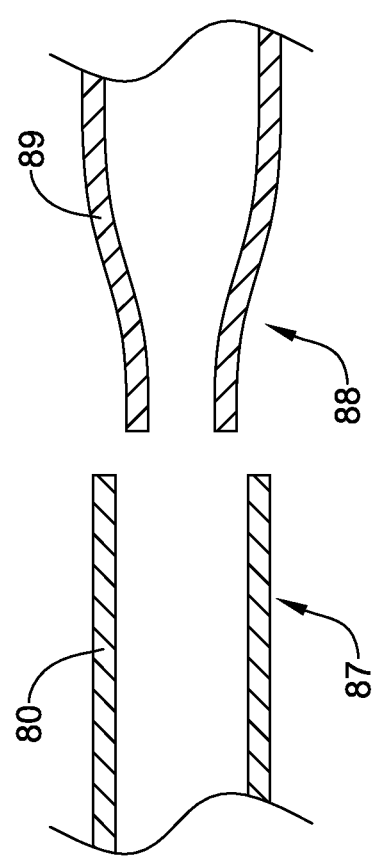
FIG. 8 shows another set of tubular elongate structures before they are joined together where the tubular elongate members are sized and shaped to facilitate the insertion of one tubular elongate member into the other tubular elongate member.

FIGS. 6-8 show several sets of tubular members that have shapes that are complementary to one another. The complementary shapes can facilitate the step of bringing the welding surfaces into close proximity by facilitating the insertion of one tubular member into the other tubular member. In FIG. 6, the second metallic tubular member 69 is shown having a smaller diameter than the first metallic tubular member 60. The difference in diameter is such that, when the second tubular member 69 is placed inside of the first tubular member 60, the coated (or the one coated and one uncoated) welding surfaces (63, 66) come into close proximity (e.g., disposed close to one another or in contact with one another). FIG. 7 shows two tubular members (70, 79) that can be similar in most respects to the tubular members of FIG. 6 and can otherwise be welded together in a similar manner. In the case of FIG. 7, the second tubular member 79 has a proximal end 75 that is formed at an angle. This angled end can facilitate the entry of the second tubular member 79 into the first tubular member 70.

Another possible embodiment of first and second tubular members (80, 89) with complementary ends is shown in FIG. 8. In this example, a proximal portion 88 of the second tubular member 89 can have a reduced diameter. This reduced diameter can facilitate to the entry of the second tubular member 89 into the first tubular member 80, similar to the manner described with respect to FIGS. 6 and 7. If the portion of the second tubular member 89 distal of the reduced diameter portion has the same outer diameter as the outer diameter of the distal portion 87 of the first tubular member 80, the transition between the first and second tubular members (80, 89) can have a substantially constant outer diameter.

The methods and structures described herein can be used in a variety of contexts, for example in the production of medical devices. As examples of medical device construction, two elongate metallic members of solid cross-section can be joined, in other medical devices two elongate metallic tubular members are joined together, in some cases one tubular member and one member of solid cross-section are joined together, and in other medical device applications metallic wires or other types of structures can be joined together.

Figure 9:
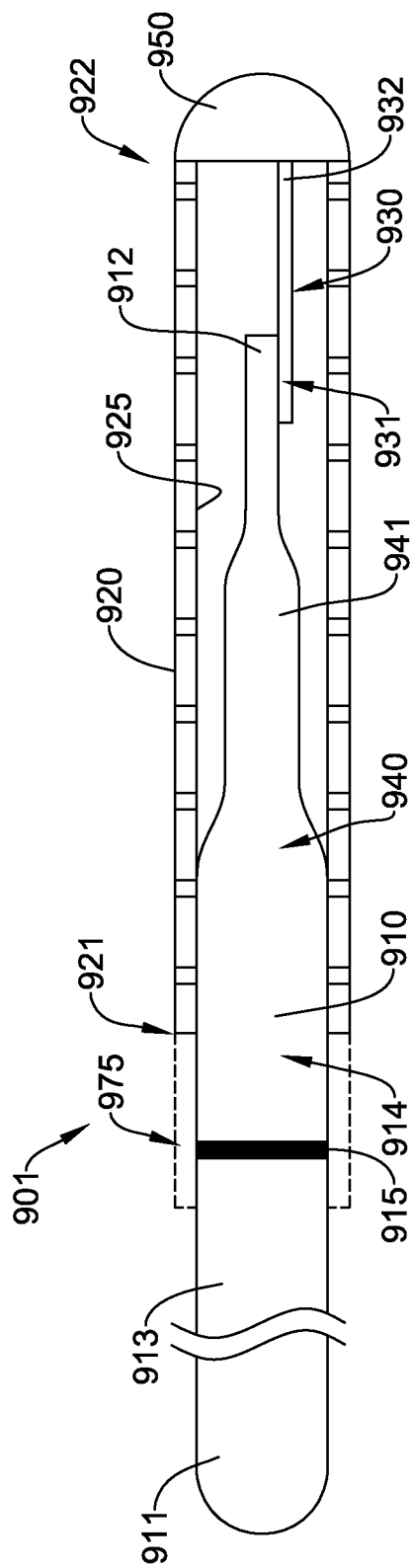
FIG. 9 shows an example of a guidewire.

Turning to FIG. 9, an example of a guidewire is shown. The guidewire 901 has a core wire 910 that is at least partially disposed within a sheath 920. The core wire can have a proximal end 911, a proximal portion 913, a distal end 912 and a distal portion 914. The proximal portion 913 can have a constant diameter and the distal portion 914 can be tapered; for example, the distal portion 914 can be tapered in a series of one or more tapered portions 940 and one or more constant diameter portions 941.

The proximal and distal portions (913, 914) can be similar in composition to any of the metallic members discussed herein. The portions (913, 914) can be joined at joint 915. For example, the proximal portion 913 can comprise iron (e.g., it can comprise stainless steel or other alloys comprising iron) and the distal portion 914 can comprise titanium (e.g., it can comprise Nitinol or other alloys comprising titanium). The joint can be, for example, any of the joints described herein. In the example shown in FIG. 9, the joint 915 is shown with a constant diameter proximal portion 913 proximal of the joint and a constant diameter portion of the distal portion 914 distal of the joint 915. The joint 915 can also be placed at different locations along the core wire 910. For example, the joint 915 could be placed at the point where the first taper 940 begins, it could be placed in the first taper 940, distal of the first taper 940, or in one of the constant diameter portions (e.g., 941) distal of the first taper 940. Also, the core wire could comprise a second joint in any of the above locations. This second joint could be similar to any of the joints described herein, and it could effectively divide the core wire 910 into proximal, intermediate and distal sections. In one embodiment, the proximal, intermediate and distal sections can alternate between metals comprising iron (e.g., stainless steel or other alloys comprising iron) and metals comprising titanium (e.g., Nitinol or other alloys comprising titanium). For example the proximal section can comprise iron (e.g., stainless steel or other alloys comprising iron), the intermediate section can comprise titanium (e.g., Nitinol or other alloys comprising titanium) and the distal section can comprise iron (e.g., stainless steel or other alloys comprising iron).

At least a portion of the core wire can be disposed within a lumen defined by a sleeve, for example a metallic sleeve 920. The sleeve 920 can have a proximal end 921, a distal end 922 and an inner surface 925. The proximal end 921 can extend proximally to a point distal of the joint 915, to the joint 915, or, as shown in phantom on FIG. 9, to a point proximal of the joint 915. The sleeve 920 can have a variable flexibility, for example by cutting slots through the sleeve 920. For examples of such tubular structures, see the disclosure of U.S. Patent Publication Nos. 2003/0060732, 2003/0069522, 2003/0009208 and 2004/0181174, all of which are hereby incorporated in their entirety.

The sleeve 920 can also comprise multiple tubular segments that have been joined together, for example in the manner described with respect to FIGS. 5-8. In some embodiments, a proximal portion of the sleeve 920 can comprise iron (e.g., it can comprise a stainless steel or other alloys comprising iron), and a distal portion of the sleeve 920 can comprise titanium (e.g., it can comprise Nitinol or other alloys comprising titanium). Also, at the point of connection between the sleeve 920 and the core wire 910, one of the sleeve 920 and the core wire 910 can comprise iron (e.g., stainless steel or other alloys comprising iron) and the other can comprise titanium (e.g., Nitinol or other alloys comprising titanium). For example, the core wire 910 at the point of connection can comprise iron (e.g., stainless steel or other alloys comprising iron) and the sleeve 920 can comprise titanium (e.g., Nitinol or other alloys comprising titanium), or vice versa.

In addition, other metallic elements can also be incorporated into the guidewire 901. For example, an extension wire 930 can be attached to the core wire distal end 912. The extension wire 930 can have a proximal portion 931 and a distal portion 932. The core wire distal end 912 and the extension wire 930 can be comprised of different metals. One of the core wire distal end 912 and the extension wire 930 can comprise iron (e.g., stainless steel or other alloys comprising iron) and the other can comprise titanium (e.g., Nitinol or other alloys comprising titanium). In one embodiment, the core wire distal end 912 can comprise Nitinol or other titanium comprising alloy and the extension wire 930 can comprise stainless steel or another iron comprising alloy, or vice versa.

The guidewire 901 can also comprise a distal tip 950. The tip 950 can be a rounded mass of material. In some examples, the rounded mass of material can be a metal. In some cases, the distal tip can be attached to the tubular member distal end 922, the core wire distal end 912 or the extension wire distal end 932, or any combination thereof. One of the distal tip 950 and the structure(s) to which the distal tip 950 is attached (e.g., the core wire distal tip, the extension wire and/or the sleeve) can comprise iron (e.g., stainless steel or other alloys comprising iron) and the other can comprise titanium (e.g., Nitinol or other alloys comprising titanium). In one embodiment, the distal tip 950 can comprise stainless steel or another iron-comprising alloy and the structure(s) to which the distal tip 950 is attached (e.g., the core wire distal tip, the extension wire and/or the sleeve) can comprise Nitinol or another titanium-comprising alloy, or vice versa.

Figure 10:
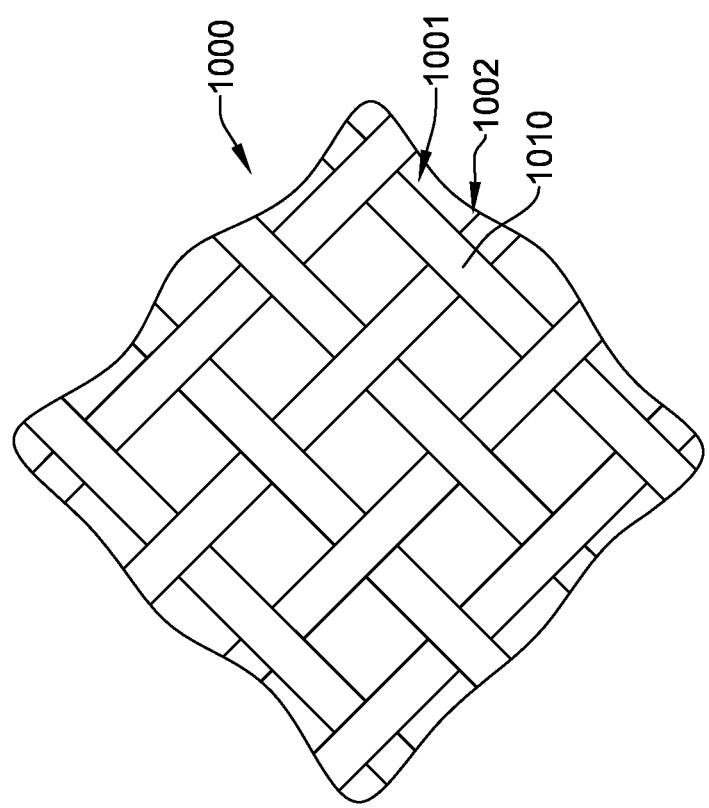
FIG. 10 shows an example of a mesh material that can be incorporated into a medical device.

Turning to FIG. 10, a portion of a mesh 1000 is shown. Mesh 1000 can be used in filters, occlusion devices, and stents, among other uses. The mesh 1000 can comprise a first strand 1001 woven together with a second strand 1002. These strands cross over one another at point 1010. In some embodiments, the strands can be attached to one another at 1010. If these strands comprise metal, the strands can be attached by welding them to one another. In some cases, one of the strands can comprise iron (e.g., stainless steel or other iron-comprising alloy) and the other strand can comprise titanium (e.g., Nitinol or other titanium-comprising alloy). In such a case, the strands can be welded together using any of the techniques described herein.

Further, it can be appreciated by one of ordinary skill in the art that multiple strands of the mesh 1000 can comprise iron (e.g., stainless steel or other alloys comprising iron) and multiple strands can comprise titanium (e.g., Nitinol or other alloys comprising titanium). At at least some of the points where strands of dissimilar material cross one another, the strands can be attached to one another using any of the welding methods described herein can be used.

Figure 11:
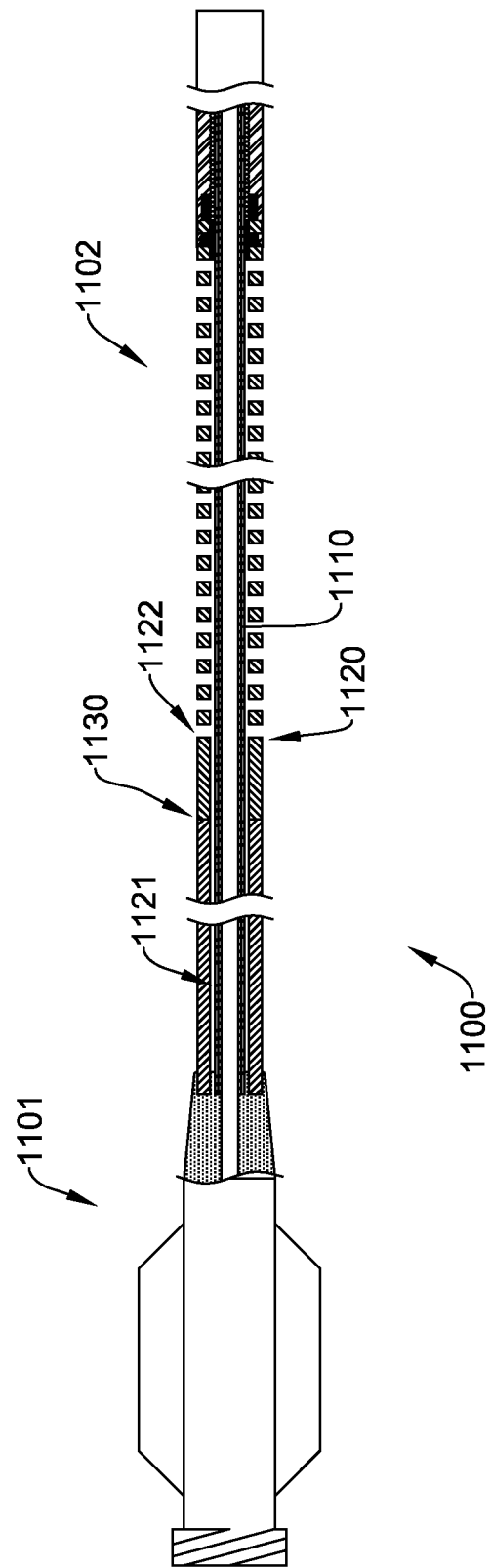
FIG. 11 shows an example of a catheter.

Turning to FIG. 11, a catheter is shown. The catheter 1100 can have a structure similar to that described in U.S. Pat. No. 7,001,369 to Griffin et al., which is incorporated herein in its entirety. The catheter 1100 can have a hub 1101 and a shaft 1102. The shaft 1102 can comprise an inner liner 1110 that can comprise a polymer. The shaft can also comprise an outer metal member 1120. The outer metal member 1120 can comprise a proximal portion 1121 and a distal portion 1122. The proximal and distal portions (1121, 1122) can be joined at a joint 1130. The joint and the proximal and distal portions can be similar to any of the joints and tubular members discussed with respect to FIGS. 5-9. One of the proximal and distal portions (1121, 1122) can comprise iron (e.g., stainless steel or other alloys comprising iron) and the other portion can comprise titanium (e.g., Nitinol or other alloys comprising titanium). For example, the proximal portion 1121 can comprise stainless steel (or other alloys comprising iron) and the distal portion 1122 can comprise Nitinol (or other alloys comprising titanium), or vice versa. Any of the welding materials and joint structures that are described with respect to FIGS. 5-9 can be used in forming the joint 1130.

The present invention should not be considered limited to the particular examples described above, but rather should be understood to cover all aspects of the invention as fairly set out in the attached claims. Various modifications, equivalent processes, as well as numerous structures to which the present invention may be applicable will be readily apparent to those of skill in the art to which the present invention is directed upon review of the instant specification. For example in some embodiments, the weld material may include a flux in addition to the components which tend to inhibit the formation of intermetallic compounds. It should be understood that this disclosure is, in many respects, only illustrative. Changes may be made in details, particularly in matters of shape, size, and arrangement of steps without exceeding the scope of the invention. The scope of the invention is, of course, defined in the language in which the appended claims are expressed.

EXAMPLES

Example 1

In this example, a series of tests were performed to understand and characterize welds of stainless steel and a nickel-titanium alloy (Nitinol) using gold as a welding material. A series of tests were completed to evaluate the strength of the welds and the effectiveness of reducing intermetallics by adding an electroplated gold layer to the welding surfaces of the materials being welded.

A heavy coat of acid gold 434 was electroplated on a stainless steel flat ribbons and a Nitinol flat ribbon. In performing the electroplating process, first, a gold strike was applied to improve adhesion and reduce the oxidation layers of the stainless steel and Nitinol, and then a gold layer was electroplated over the strike. The plating material used was electrolytic soft gold called Technic ACR 434. The parameters for the gold strike process and the gold plating process are outlined in Table 1 below.

TABLE 1

| Chemistry | HCl Strike | HCl Strike | HF Strike | HF Strike |
|---|---|---|---|---|
| Gold Strike Process | | | | |
| Gold Strike Temp | 110 F. | 110 F. | room | room |
| Gold Strike Current | 0.015 A | 0.015 A | 0.015 A | 0.015 A |

TABLE 1-continued

| Chemistry | HCl Strike | HCl Strike | HF Strike | HF Strike |
|---|---|---|---|---|
| Gold Strike time | 3 min | 3 min | 3 min | 3 min |
| Agitation | 3 | 3 | 3 | 3 |
| Gold Plating Process | | | | |
| Plating Temp | 150 F. | 150 F. | 150 F. | 150 F. |
| Plating Current | 0.08 A | 0.08 A | 0.08 A | 0.08 A |
| Plating time | 12 min | 12 min | 12 min | 12 min |
| Agitation | 2 | 2 | 2 | 2 |
| Plating Thickness | 700 ± 200 microinch | 700 ± 200 microinch | 700 ± 200 microinch | 700 ± 200 microinch |

Then, the plated stainless steel flat ribbon was laser welded to the Nitinol flat ribbon in a lap joint configuration, and the welded structures were tested for tensile and fatigue strengths. The result of the testing is shown in Table 2 below:

TABLE 2

| Joint Type | Plating Material (Weld material) | Tensile Strength (goal = 3 lbf.) | Fatigue cycles (goal = 10 to 20 cycles) |
|---|---|---|---|
| Lap welded flat ribbons | Au | 9.064 lbf. | 306 cycles |

SEM and metallographic analysis was also conducted on the welded parts and revealed a good transition between the two different metals (stainless steel and Nitinol) without demarcation lines, implying a good weld joint.

Example 2

In this example, a series of tests were performed to understand and characterize welds of stainless steel and a nickel-titanium alloy (Nitinol) using a combination of gold and nickel as welding materials. A series of tests were completed to evaluate the strength of the welds and the effectiveness of reducing intermetallics by adding an electroplated gold layer and an electroplated nickel layer to the welding surfaces of the materials being welded.

A heavy coat of acid gold 434 was electroplated on a stainless steel flat ribbon and stainless steel round wire, and a Nitinol flat ribbon and a Nitinol round wire. In performing the electroplating process, first, a gold strike was applied to improve adhesion and reduce the oxidation layers of the stainless steel and Nitinol, and then a gold layer was electroplated over the strike. Thereafter, a nickel layer was electroplated over the gold layer. The gold plating material used was electrolytic soft gold called Technic ACR 434. The nickel plating material used was low-phosphorus nickel. The parameters for the gold strike process, the gold plating process, and the nickel plating process are outlined in Table 3 below. The nickel was added to enhance the laser welding and to reduce high reflectivity produced by the gold. Either electroplated material is capable to reduce the intermetallic layer often formed during fusion when the dissimilar materials are welded.

TABLE 3

| Chemistry | HCl Strike | HCl Strike | HF Strike | HF Strike |
|---|---|---|---|---|
| Gold Strike Process | | | | |
| Gold Strike Temp | 110 F. | 110 F. | room | room |
| Gold Strike Current | 0.015 A | 0.015 A | 0.015 A | 0.015 A |
| Gold Strike time | 3 min | 3 min | 3 min | 3 min |
| Agitation | 3 | 3 | 3 | 3 |
| Gold Plating Process | | | | |
| Plating Temp | 150 F. | 150 F. | 150 F. | 150 F. |
| Plating Current | 0.08 A | 0.08 A | 0.08 A | 0.08 A |
| Plating time | 12 min | 12 min | 12 min | 12 min |
| Agitation | 2 | 2 | 2 | 2 |
| Plating Thickness | 700 ± 200 microinch | 700 ± 200 microinch | 700 ± 200 microinch | 700 ± 200 microinch |
| Nickel Plating Process | | | | |
| Plating Temp | — | room | — | room |
| Plating Current | — | 0.009 A | — | 0.009 A |
| Plating time | — | 10 min | — | 10 min |
| Agitation | — | 4 | — | 4 |
| Plating Thickness | — | 200 ± 100 microinch | — | 200 ± 100 microinch |

Then, the plated stainless steel flat ribbon was laser welded to the Nitinol flat ribbon in a lap joint configuration, and the welded structures were tested for tensile and fatigue strengths. The plated stainless steel round wire was laser welded to the Nitinol round wire in a butt joint configuration, and the welded structures were tested for tensile and fatigue strengths. The result of the testing is shown in Table 4 below:

TABLE 4

| Joint Type | Plating Material (Weld material) | Tensile Strength (goal = 3 lbf.) | Fatigue cycles (goal = 10 to 20 cycles) |
| --- | --- | --- | --- |
| Lap welded flat ribbons | Au + Ni | 12.894 lbf. | 154 cycles |
| Butt welded round wires | Au + Ni | 11.69 lbf. | 493 cycles |

SEM and metallographic analysis was also conducted on the welded parts and revealed a good transition between the two different metals (stainless steel and Nitinol) without demarcation lines, implying a good weld joint.

We claim:

1. A method of manufacturing a medical device, the method comprising:
   providing a first elongate metallic member comprising stainless steel and having a first welding surface;
   providing a second elongate metallic member comprising nickel-titanium alloy and having a second welding surface;
   applying a welding material to at least one of the welding surfaces;
   disposing the first welding surface proximate the second welding surface; and
   welding the welding surfaces and the welding material, forming a joint between the metallic members;
   wherein the welding material comprises a metal carbide in which the metal has an affinity for carbon that is weaker than that of titanium for carbon or a metal nitride in which the metal has an affinity for nitrogen that is weaker than that of titanium for nitrogen.

2. The method of claim 1, wherein the welding surfaces and the welding material are melted during the welding step and the molten materials are intermixed to form the weld.

3. The method of claim 1, wherein the welding material inhibits the formation of brittle intermetallic iron-titanium compounds during the welding step.

4. The method of claim 1, wherein the welding material is applied on at least one of the welding surfaces using a vapor deposition process.

5. The method of claim 1, wherein the welding material is applied on at least one of the welding surfaces using an electrodeposition process.

6. The method of claim 1, wherein the welding material is applied on at least one of the welding surfaces as a paste-like substance that is spread on at least one of the surfaces.

7. The method of claim 1, wherein the welding material further comprises nickel.

8. The method of claim 1, wherein the joint comprises titanium carbide.

9. The method of claim 1, wherein the joint comprises titanium nitride.

10. The method of claim 1, wherein the weld joint contains titanium carbide, titanium nitride or titanium carbonitride.

11. A method of forming a joint, the method comprising:
    providing a first metallic member comprising a first alloy comprising iron, the first member having a first welding surface;
    providing a second metallic member comprising a second alloy comprising titanium, the second member having a second welding surface;
    applying a welding material to at least one of the welding surfaces, the welding material comprising a metal carbide in which the metal has an affinity for carbon that is weaker than that of titanium for carbon or a metal nitride in which the metal has an affinity for nitrogen that is weaker than that of titanium for nitrogen; and
    welding the welding surfaces and the welding material, forming a joint between the first and second metallic members;
    wherein the welding material inhibits the formation of the brittle iron-titanium compounds within the joint.

12. The method of claim 11, wherein the joint comprises at least one of titanium carbide and titanium nitride.

13. A medical device comprising:
    a first metallic member comprising stainless steel;
    a second metallic member comprising a nickel-titanium alloy; and
    a weld joint formed between the welding surfaces of the first and second metallic members, the joint comprising components of stainless steel, nickel-titanium, and a welding material comprising a metal carbide in which the metal has an affinity for carbon that is weaker than that of titanium for carbon or a metal nitride in which the metal has an affinity for nitrogen that is weaker than that of titanium for nitrogen.

* * * * *